US00PP08598P

United States Patent [19]

Lopez

[11] Patent Number: Plant 8,598

[45] Date of Patent: Feb. 15, 1994

[54] STRAWBERRY PLANT NAMED CARTCUA

[75] Inventor: Jose M. A. Lopez, Tudela-Navarra, Spain

[73] Assignee: Plantas de Navarra, S.A., Valtierra, Spain

[21] Appl. No.: 901,384

[22] Filed: Jun. 19, 1992

[51] Int. Cl.[5] ..... A01H 5/00

[52] U.S. Cl. ..... Plt./48

[58] Field of Search ..... Plt. 48, 49

*Primary Examiner*—James R. Feyrer

*Attorney, Agent, or Firm*—Christie, Parker & Hale

[57] ABSTRACT

A strawberry plant producing almost cylindrically shaped fruit and having inflorescence extending above the foliage.

3 Drawing Sheets

BACKGROUND OF THE INVENTION

The new variety of strawberry was created in a breeding program by my crossing two parents from among a group of seedlings which were obtained from a free pollenization of 32 different varieties and seedlings; in particular, by crossing as seed parent a variety designated 86-189 and as a pollen parent a variety designated 86-210. Both parental varieties are proprietary and have not been commercialized.

The resulting seedling of the new variety was grown and asexually propagated by stolens in Soria, Spain. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present inventon relates to a new and distinct strawberry variety. The varietal denomination of the new variety is 'Cartcua'. Among the characteristics which distinguish the new variety from other varieties of which I am aware are a combination of traits which include inflorescence that appears above the foliage and abundant production of bright colored, almost cylindrically shaped fruit.

COMPARISON TO CLOSEST VARIETY

The new variety is closest to the variety 'Selva', but is distinguished therefrom by the following characteristics possessed by 'Cartcua' which are different than, or not possessed by, 'Selva':

1. In the new variety hairs extend obliquely towards the top of the petiole.
2. The blistering of the leaves of 'Cartcua' is stronger.
3. In the new variety the inflorescence appears on the top of the foliage.
4. The calyx of 'Cartcua' is larger than the corolla and the mature fruit are long and almost cylindrically shaped.
5. The shape of the teeth of the terminal leaflet are nearly round.
6. In fruit the achenes are depressed.
7. The color of the fruit is weaker. Further information regarding the variety 'Selva' is available in U.S. Plant Pat. No. 5,266.

BRIEF DESCRIPTION OF THE ILLUSTRATIONS

The accompanying photographs show typical specimens of the new variety, including fruit, foliage and flower, in color as nearly true as it is reasonably possible to make in color illustrations of this character.

One illustration shows typical fruit in cross section illustrating the typical flesh and flesh coloration, conspicuous core and core cavity and almost cylindrical shape;

Another shows whole and sliced, detached fruit;

Another illustration shows the fruit against the background of the top surface of the foliage;

A fourth illustration shows the flower and reproductive organs of the new variety; and A fifth illustration shows the top and undersurface of a typical foliole of the new variety.

DESCRIPTION OF THE NEW VARIETY

The following detailed description of the new variety is based upon observations taken of plants and fruit grown "underglass", i.e., undertunnel, in the farm of La Mogalla in Cartaya (Huelva), Spain. This description is in accordance with UPOV terminology and the color terminology herein is in accordance with the The Royal Horticultural Society Colour Chart (R.H.S.C.C.) and the color descriptions refer to plate numbers in the aforementioned color chart. Color designations, color descriptions and other phenotypical descriptions may deviate from the stated values and descriptions depending upon variation in environmental, seasonal, climatic and cultural conditions.

Propagation

The new variety is principally propagated by way of stolens. Although propagation by stolens is presently preferred, other known methods of propagating strawberry plants may be employed. It has been determined that the plants root well after transplanting.

The following additional information is provided to further describe the new variety.

Plant:

*Habit.*—Flat, globose.
*Density.*—Medium.
*Vigor.*—Medium.
*Height.*—About 12 cm.
*Width.*—About 28 cm.

Foliage:

*Leaf.*—Color: Upper side — Near 136B. Underside — Near 139B to 136C. Cross section: Slightly convex. Blistering: Strong texture or rugosity. Number of leaflets: Only three. Length: About 8 cm. Width: About 10.5 cm.

*Terminal leaflet (length to width ratio).*—Longer than broad. Length — About 5.5 cm. Width — About 5.5 cm.

*Terminal leaflet (shape of base).*—Acute.

*Terminal leaflet (shape of teeth).*—Rounded.

*Petiole.*—Pose of hairs: Upwards. Length of petiole about 7.5 cm.

*Stipules.*—Anthocyanin. Coloration: Weak.

*Stolens.*—Number: Medium. Anthocyanin coloration: Weak (light). Thickness: Medium. Pubescence: Weak.

Flower:

*Size.*—Large; primary flower about 4.5 cm, secondary flower about 2.5 cm.

*Size of calyx relative to corolla.*—Larger.

*Size of inner calyx relative to outer.*—Same size.

*Spacing of petals.*—Overlapping.

*Petal length to width ratio.*—As long as broad.

*Petal color.*—White.

*Separation of the petals of flowers with 5 or 6 petals.*—Overlapping each other.

*Fruiting truss.*—Attitude (at first picking): Semi-erect.

*Inflorescence.*—Above foliage.

Fruit:

*Ratio of length to maximum width.*—Much longer than broad.

*Size.*—Very large. Primary fruit — Length about 7 cm, width about 4.5 cm. Secondary fruit — Length about 5 1 cm, width about 4 cm.

*Predominant shape.*—Narrow, conical and elongated, approaching cylindrical; normally much longer than broad; some fruit mildly furrowed, some fruit having a wedge shape at the apex, nearly as broad as the shoulders of the fruit.

*Difference in shapes between primary and secondary fruits.*—Moderate.

*Band without achenes.*—Narrow.

*Unevenness of surface.*—Medium.

*Color.*—Orange red, near 34B.

*Evenness of color.*—Slightly uneven.

*Glossiness.*—Strong.

*Insertion of achenes.*—Below surface.

*Insertion of calyx.*—Set above fruit.

*Pose of the calyx segments.*—Reflexed.

*Size of calyx in relation to fruit diameter.*—Larger.

*Adherence of calyx.*—Medium.

*Firmness.*—Firm.

*Color of flesh.*—Near 33C to 34C, medium red.

*Evenness of color of the flesh.*—Even.

*Sweetness.*—Medium.

*Acidity.*—Medium.

*Time of flowering (50% of plants at first flower).*—Early.

*Time of ripening (50% of plants with ripe fruits).*—Early.

*Type of bearing.*—Partially remontant.

*Fruiting (La Mogalla, Spain).*—For plants planted October 21, about 10% flowering by about December 16, first mature fruit about January 27 and maturity (15-20 gm/plant) about February 9.

I claim:

1. A new and distinct variety of strawberry, substantially as shown and described.

* * * * *

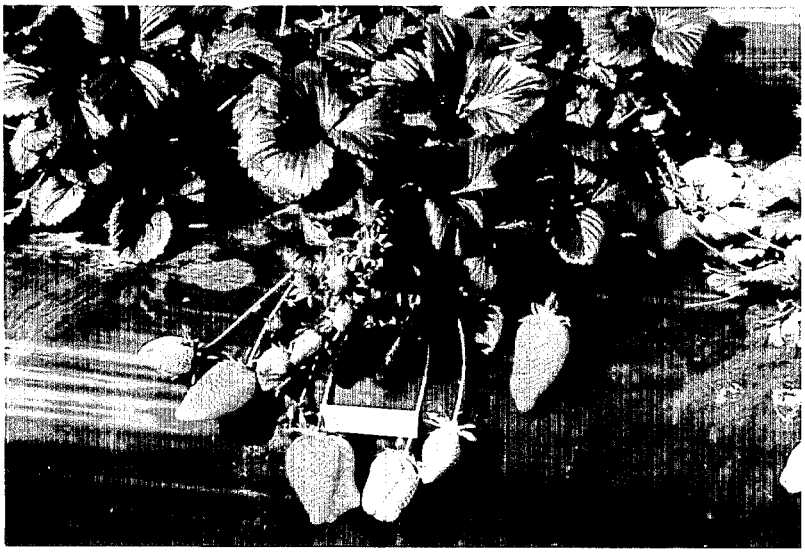

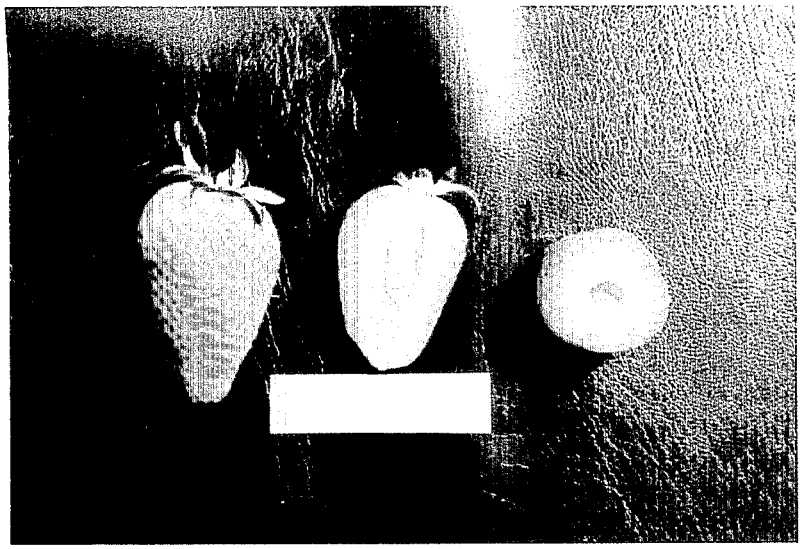
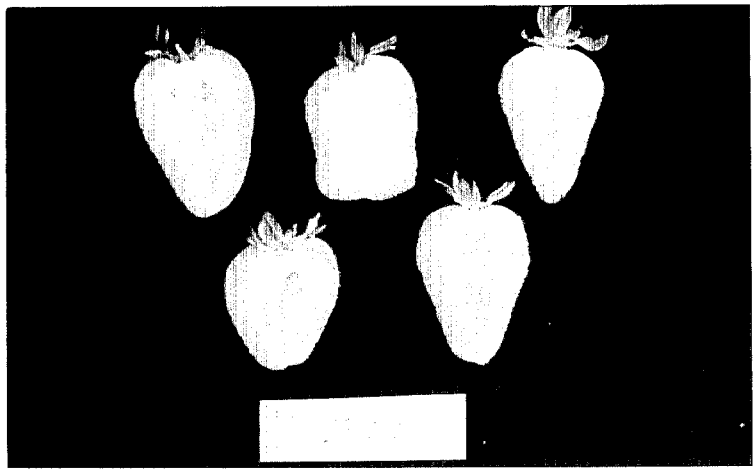

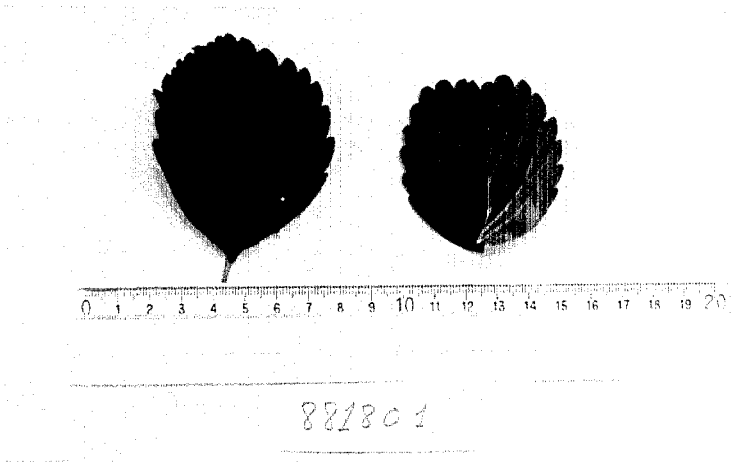
0 1 2 3 4 5 6 7 8 9 10 11 12 13 14 15 16 17 18 19 20
881801
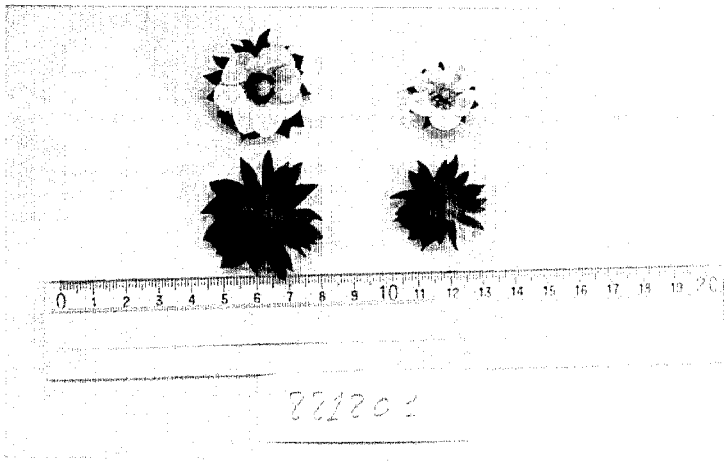
0 1 2 3 4 5 6 7 8 9 10 11 12 13 14 15 16 17 18 19 20
881801

UNITED STATES PATENT AND TRADEMARK OFFICE

CERTIFICATE OF CORRECTION

PATENT NO. : Plant 8,598

DATED : February 15, 1994

INVENTOR(S) : Jose M.A. Lopez

It is certified that error appears in the above-indentified patent and that said Letters Patent is hereby corrected as shown below:

On the Cover Page:

[56] References Cited, U.S. PATENT DOCUMENTS, after "[58]" insert the following references:

-- [56] References Cited

U.S. PATENT DOCUMENTS

| | | |
|---|---|---|
| P.P. 5,266 | 7/1984 | Bringhurst et al..Plt.49 |
| P.P. 7,614 | 8/1991 | Bringhurst et al..Plt.49 |
| P.P. 7,881 | 6/1992 | Izsak et al.....Plt.48 |

--.

Column 2, line 27, before "Royal" delete "The".

Signed and Sealed this

First Day of November, 1994

Bruce Lehman

*Attest:*

BRUCE LEHMAN

*Attesting Officer*

*Commissioner of Patents and Trademarks*